United States Patent [19]
Yamamoto et al.

[11] Patent Number: 5,306,629
[45] Date of Patent: Apr. 26, 1994

[54] METHOD FOR PRODUCING DINUCLEOSIDE POLYPHOSPHATE, NUCLEOSIDE POLYPHOSPHATE OR DERIVATIVES THEREOF

[75] Inventors: Hideki Yamamoto; Mika Manabe; Hiroshi Nakajima, all of Kyoto, Japan

[73] Assignee: Unitika Ltd., Hyogo, Japan

[21] Appl. No.: 45,877

[22] Filed: Apr. 15, 1993

[30] Foreign Application Priority Data

Apr. 17, 1992 [JP] Japan ............................ 4-125668

[51] Int. Cl.⁵ .................... C12P 19/38; C12P 19/34; C12N 9/10
[52] U.S. Cl. ........................... 435/87; 435/41; 435/88; 435/90; 435/193; 435/194; 435/832; 435/942
[58] Field of Search ............. 435/41, 87, 88, 90, 435/193, 194, 832, 942

[56] References Cited

U.S. PATENT DOCUMENTS 4,971,903  11/1990  Hyman ........................ 435/6

OTHER PUBLICATIONS

F. Grummt, Pro. N.A.S., 75, 371 (1978).
P. F. Maness et al., J. Biol. Chem., 258, 4055 (1983).
M. J. Harrison et al., FEBS Letters, 54, 57 (1975).
O. Goerlich et al., Eur. J. Biochem., 126, 135 (1982).
A. Guranowski et al., Biochemistry, 27, 2959 (1988).

*Primary Examiner*—Herbert J. Lilling
*Attorney, Agent, or Firm*—Sughrue, Mion, Zinn, Macpeak & Seas

[57] ABSTRACT

A method for producing a dinucleoside polyphosphate, a nucleoside polyphosphate or a derivative thereof which comprises using adenosine-5'-triphosphate, polyphosphate or a derivative thereof and a sulfate as reaction substrates and forming a dinucleoside polyphosphate, nucleoside polyphosphate or derivatives thereof via a two-stage reaction through the use of two enzymes, namely, adenosine-5'-triphosphate sulfurylase and diadenosine tetraphosphate phosphorylase as catalysts. Further, another method for producing a dinucleoside polyphosphate, a nucleoside polyphosphate or a derivative thereof which comprises using adenosine-5'-triphosphate, polyphosphate or a derivative thereof and a sulfate as reaction substrate in the presence of an enzyme capable of converting adenosine-5'-diphosphate into adenosine-5'-triphosphate, and forming the dinucleoside polyphosphate, nucleoside polyphosphate or derivatives thereof via a two-stage reaction through the use of two enzymes, namely, adenosine-5'-triphosphate sulfurylase and diadenosine tetraphosphate phosphorylase as catalysts is provided. According to the present invention, highly pure dinucleoside polyphosphate, nucleoside polyphosphate or derivatives thereof can be produced at a high yield and these products can be easily isolated and purified.

15 Claims, No Drawings

METHOD FOR PRODUCING DINUCLEOSIDE POLYPHOSPHATE, NUCLEOSIDE POLYPHOSPHATE OR DERIVATIVES THEREOF

FIELD OF THE INVENTION

This invention relates to a method for producing a dinucleoside polyphosphate, a nucleoside polyphosphate or a derivative thereof which are useful as drugs or starting materials therefor.

BACKGROUND OF THE INVENTION

Diadenosine polyphosphate or derivatives thereof have physiological functions which include promoting DNA synthesis in BHK cells suffering from G1 inhibition as disclosed in F. Grummt, Pro. N.A.S., 75, 371 (1978), inhibiting phosphorylation as disclosed in P. F. Maness et al., J. Biol. Chem., 258, 4055 (1983), and inhibiting platelet aggregation as disclosed in M. J. Harrison et al., FEBS Letters, 54, 57 (1975). Thus, nucleoside polyphosphates (hereinafter referred to simply as NpnN') such as diadenosine polyphosphate or nucleoside polyphosphates (hereinafter referred to simply as pnN) and derivatives thereof are known for their use as drugs and starting materials therefor.

Regarding methods for obtaining this diadenosine polyphosphate or derivatives thereof, O. Goerlich et al., Eur. J. Biochem., 126, 135 (1982) reports that diadenosine tetraphosphate is synthesized from adenosine-5'-triphosphate (hereinafter referred to simply as ATP) while dideoxyadenosine tetraphosphate, which is a derivative of diadenosine tetraphosphate, is synthesized from 2'-deoxyadenosine-5'-triphosphate, which is a derivative of ATP. These products are synthesized by using various aminoacyl-tRNA synthetases such as lysyl-tRNA synthetase, histidyl-tRNA synthetase and phenylalanyl-tRNA synthetase each originating in *Escherichia coli*, lysyl-tRNA synthetase and phenylalanyl-tRNA synthetase each originating in yeasts, phenylalanyl-tRNA synthetase originating in Fusarium and phenylalanyl-tRNA synthetase originating in sheep hepatic cells.

In the above-mentioned method wherein ATP or a derivative thereof is reacted with an amino acid under the catalytic action of each aminoacyl-tRNA synthetase to thereby synthesize NpnN', incubated microorganisms or hepatic cells are disrupted and the target enzyme is purified to obtain the aminoacyl-tRNA to be used as a catalyst. However, since microorganisms or cells occurring in nature contain only an extremely small amount of the aminoacyl-tRNA synthetase, there is a disadvantage that a large amount of microorganisms must be incubated or a large amount of cells must be prepared for producing the NpnN'.

Another method for synthesizing NpnN' by reacting ATP or its derivative with adenosine-5'-phosphosulfate (hereinafter referred to simply as APS) under the catalytic action of diadenosine tetraphosphate phosphorylase (hereinafter referred to simply as Ap4A phosphorylase) was proposed by A. Guranowski et al., Biochemistry, 27, 2959 (1988). The method wherein APS is used suffers from some problems such that the APS starting material is unstable and expensive. Moreover, the ATP or its derivative (ATP is used in the above reference) is converted into NpnN' (ApnN' is used in the above reference) only at a low rate, which causes practical problems for synthesizing the NpnN' from ATP or a derivative thereof.

SUMMARY OF THE INVENTION

An object of the present invention is to provide a method whereby highly pure NpnN', pnN or a derivative thereof can be easily obtained at a high yield, thus solving the above-mentioned problems.

In order to solve these problems, the present inventors have conducted extensive studies. As a result, they have successfully found that NpnN', pnN or a derivative thereof can be unexpectedly produced at a high conversion ratio by reacting ATP, polyphosphate, or a derivative thereof with a sulfate as reaction substrates in the presence of ATP sulfurylase and Ap4A phosphorylase. The highly pure NpnN', pnN or a derivative thereof can also be produced at a high yield by performing the above-mentioned reaction with the additional presence of an enzyme capable of converting adenosine-5'-diphosphate (hereinafter referred to simply as ADP) into ATP. The present invention has been accomplished based on these findings.

Accordingly, the present invention provides a method for producing NpnN', pnN or a derivative thereof which comprises using ATP, polyphosphate, or derivatives thereof and a sulfate as reaction substrates and forming NpnN', pnN or a derivative thereof via a two-stage reaction through the use of two enzymes, i.e., ATP sulfurylase and Ap4A phosphorylase, and another method for producing NpnN', pnN or a derivative thereof which comprises using ATP, polyphosphate, or derivatives thereof and a sulfate as reaction substrates in the presence of an enzyme capable of converting ADP into ATP and forming NpnN', pnN or a derivative thereof via a two-stage reaction through the use of two enzymes, i.e., ATP sulfurylase and Ap4A phosphorylase.

DETAILED DESCRIPTION OF THE INVENTION

The present invention will be described in greater detail hereinafter.

A method for producing Ap4A from ATP, which is cited as an example of the enzyme reaction of the present invention relating to the formation of NpnN', pnN or a derivative thereof, may be represented by the following steps 1 and 2. It is a two-stage reaction involving (1) the sulfation of ATP from ATP and a sulfate, under the catalytic action of ATP sulfurylase to form APS, and (2) the formation of Ap4A from the APS thus formed and ATP, under the catalytic action of Ap4A phosphorylase.

It is preferable to simultaneously use an enzyme capable of hydrolyzing pyrophosphoric acid into phosphoric acid, i.e., pyrophosphatase (hereinafter referred to simply as PPase) in order to further displace the equilibrium of the reaction to the formation of Ap4A.

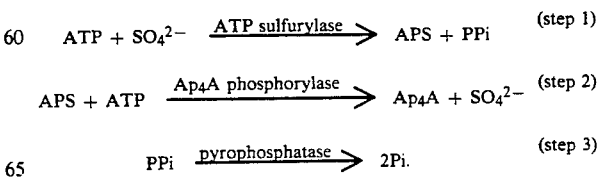

Examples of the nucleoside moieties of NpnN' (i.e., N and N') include adenosine, guanosine, deoxyadenosine, and deoxyguanosine. Among them, adenosine and guanosine are preferable, and adenosine is the most preferable.

The term "derivatives of NpnN'" as used herein means compounds having the structure of NpnN' as a basic skeleton and being derived from ATP or derivatives thereof. If adenosine is taken as an example of the nucleoside moiety, examples of such NpnN' derivatives include alkylated, carboxyalkylated, benzoylated or carboxybenzoylated derivatives at the N6-position of adenine ring, halogenated derivatives at adenine ring, hydroxy derivatives, deamino derivatives, deoxyamino derivatives, $N^6,N^6$-dicarboxymethyladenosine tetraphosphate and pentaphosphate, $N^6,N^6$-dicarboxyethyladenosine tetraphosphate and pentaphosphate, $N^6,N^6$-(P-dicarboxybenzoyl)adenosine tetraphosphate and pentaphosphate, di(8-bromadenosine) tetraphosphate and derivatives of these compounds.

Examples of the nucleoside moiety of pnN (i.e., N) include adenosine, guanosine, deoxyadenosine, and deoxyguanosine. Among them, adenosine and guanosine are preferable, and adenosine is the most preferable.

The term "derivatives of pnN" as used herein means compounds having the structure of pnN as a basic skeleton and being derived from ATP or derivatives thereof. If adenosine is taken as an example of the nucleoside moiety, examples of such pnN derivatives include alkylated, carboxyalkylated, benzoylated or carboxybenzoylated derivatives at the N6-position of adenine ring, halogenated derivatives at adenine ring, hydroxy derivatives, deamino derivatives, deoxyamino derivatives, $N^6,N^6$-dicarboxymethyladenosine tetraphosphate and pentaphosphate, $N^6,N^6$-dicarboxyethyladenosine tetraphosphate and pentaphosphate, $N^6,N^6$-(P-dicarboxybenzoyl)adenosine tetraphosphate and pentaphosphate, di(8-bromadenosine) tetraphosphate and derivatives of these compounds.

The derivatives of ATP used in the process of the present invention are nucleoside triphosphates of which nucleoside moiety corresponds to the nucleoside moiety of NpnN' or derivatives thereof mentioned above.

The only requirement of the ATP sulfurylase and the Ap$_4$A phosphorylase of the present invention is that they can synthesize Ap$_4$A when combined together. Examples of the ATP sulfurylase and the Ap$_4$A phosphorylase include enzymes originating in yeasts such as *Saccharomyces cerevisiae* (e.g., IFO 1008 deposited at the Institute for Fermentation, Osaka, 17-85, Jyusohonmachi 2-chome, Yodogawa-ku, Osaka, Japan) and those originating in thermophilic bacteria belonging to the genus Bacillus or Thermus such as *Bacillus stearothermophilus* (e.g., NCA 1503 strain, ATCC 29609 deposited at the American Type Culture Collection, 12301 Parklawn Drive Rockville, Md. 20852, U.S.A.) and *Bacillus coagulans* (e.g., ATCC 7050 strain deposited at the American Type Culture Collection, 12301 Parklawn Drive Rockville, Md. 20852, U.S.A.). In addition, enzymes originating in *Escherichia coli* (e.g., JM101Tr, Y1089, IBPC111) and *Saccharomyces cerevisiae* (e.g., CMY214) may be used as the Ap$_4$A phosphorylase, while enzymes originating in *Penicillium chrysogenum* (e.g., IFO 4626 deposited at the Institute for Fermentation, Osaka, 17-85, Jyusohonmachi 2-chome, Yodogawa-ku, Osaka, Japan), *Aspergillus niger* and *Neurospora crassa* may be used as the ATP sulfurylase. Furthermore, bacteria having the genes of these microorganisms introduced therein can also be used to obtain these enzymes. The enzyme originating in *Saccharomyces cerevisiae* (IFO 1008) is preferable as the Ap$_4$A phosphorylase, and the enzyme originating in *Bacillus stearothermophilus* (NCA 1503 strain, ATCC 29609) is preferable as the ATP sulfurylase.

In the present invention, the highly pure reaction product can be produced at a high yield by the presence of an enzyme capable of converting ADP into ATP. An enzyme capable of converting a ADP derivative into a corresponding ATP derivative may also be used depending on the starting material used. A number of enzymes such as acetate kinase, carbamate kinase, creatine kinase, 3-phospho-glycerate kinase, pyruvate kinase and polyphosphate kinase may be employed as the enzyme capable of converting ADP into ATP to be used in the present invention. It is preferable to use acetate kinase since it can be easily obtained.

Examples of enzymes capable of converting ADP into ATP include enzymes originating in *Escherichia coli*, enzymes originating in yeasts and enzymes originating in thermophilic bacteria of the genus Bacillus or Thermus.

Any PPase such as the commercially available PPase, PPase extracted from a microorganism, etc. can be used in the present invention so long as the enzyme can convert PPi into 2Pi. Examples of the PPase originated in a microorganism include those originated in *Escherichis coli*, yeasts, thermophilic bacteria of the genus Bacillus or Thermus, etc.

The *Escherichia coli*, yeasts and bacteria of the genus Bacillus or Thermus can be incubated by a known method as described, for example, in U.S. Pat. No. 5,094,947.

Nutrient mediums used for incubating bacterium in the present invention may comprise a carbon source selected from among, for example, sugars such as glucose, sucrose, fructose, starch hydrolysate, molasses and sulphite waste liquor, organic acids such as acetic acid and lactic acid, and furthermore, alcohols, fats, fatty acids and glycerol which can be metabolized by the bacterium, and a nitrogen source selected from a group including inorganic and organic substances such as ammonium sulfate, ammonium chloride, ammonium phosphate, ammonia, amino acids, peptone, meat extract and yeast extract. The nutrient medium may further contain inorganic salts selected from a group including potassium, sodium, phosphoric acid, zinc, iron, magnesium, manganese, copper, calcium and cobalt salts. Moreover, it may contain a trace amount of metal salts, corn steep liquor, vitamins and nucleic acids. Nutrient mediums commonly employed for bacteria (e.g., the medium described in U.S. Pat. No. 5,094,947, etc.) may be used therefor.

The bacterium may be incubated in such a medium under aerobic conditions at 10° to 80 °C. for 2 to 6 hours.

The above-mentioned three enzymes can be obtained from the bacterium in the following manner. First, the bacterium are collected from the culture and then disrupted by using, for example, a homogenizer, a blender, a dynomill, a French press, by ultrasonic treatment, a freezing and thawing method, or treatment with lysozyme.

Next, a cationic polymer agglutinator is added to the disrupted cell suspension (cell extract) thus obtained to thereby precipitate disrupted cell fragments and nucleic acids.

Examples of the cationic polymer agglutinator used herein include polyaminoalkyl methacrylates, polyaminoalkyl methacrylate/acrylamide copolymers, Mannich's denatured polyacrylamides, polydimethylallylammonium salts, polyvinylimdazolines, polyacrylamides, and amine-series polycondensates.

The amount of the polymer agglutinator added varies depending on the type of agglutinator. Preferably, the agglutinator is added in an amount of from 1 to 40 parts by weight per 100 parts by weight of the disrupted microorganism on a dry basis. The cationic polymer agglutinator is previously dissolved in water and then added to the disrupted cell suspension, followed by stirring for 10 minutes to 24 hours.

If it is necessary to control the pH value, a buffer may be appropriately added thereto in such an amount so as to give a concentration of 10 to 200 mM. Alternatively glucose may be added in an amount of from 1 to 50 parts by weight per 100 parts by weight of the disrupted cell suspension to stabilize the protein.

Subsequently, the disrupted cell fractions and nucleic acids thus precipitated are separated by, methods such as allowing it to stand, centrifugation or filtration.

Thus, a crude enzyme preparation can be obtained. In order to further purify the enzyme preparation, various chromatographic procedures such as gel filtration chromatography, hydrophobic chromatography, affinity chromatography and ion exchange chromatography may be employed.

In the method for producing NpnN', pnN or a derivative thereof according to the first embodiment of the present invention, buffer, ATP, polyphosphate, or its derivative, sulfate ion ($SO_4^{2-}$), magnesium ion ($Mg^{2+}$), ATP sulfurylase and Ap$_4$A phosphorylase may be fed into a single reactor in order to initiate the reaction. Further, PPase may be added thereto so as to aid the performance of the reaction, if necessary.

In the method for producing NpnN', pnN or a derivative thereof according to the second embodiment of the present invention, buffer, ATP, polyphosphate, or its derivative, sulfate ion ($SO_4^{2-}$), magnesium ion ($Mg^{2+}$), ATP sulfurylase, Ap$_4$A phosphorylase, an enzyme capable of converting ADP into ATP and a phosphate donor may be fed into a single reactor in order to initiate the reaction. Further, PPase may be added thereto so as to aid the performance of the reaction, if necessary.

The reactor to be used herein may be arbitrarily selected, so long as the reaction can proceed efficiently therein. The size and shape of the reactor may be determined depending on the amount of each enzyme, the substrate concentration, the pH value, the feeding rate and the reaction temperature. Types of reactors include a membrane-type reactor or a column-type reactor may be used therefor. A membrane-type reactor can be effectively used since the enzymes, which are high molecular weight substances, can be kept in the reactor.

When a column-type reactor is used, the enzymes may be bound to, included in, or adsorbed by, an appropriate carrier selected from among, for example, derivatives of polysaccharides such as cellulose, dextran and agarose, vinyl polymer derivatives such as polystyrene, ethylene/maleic acid copolymer and crosslinked polyacrylamide, polyamino acid or amide derivatives such as L-alanine/L-glutamic acid copolymer and polyaspartic acid and inorganic derivatives such as glass, alumina, and hydroxyapatite, and then packed in the column in the form of a so-called immobilized enzyme.

These reactors are described with the assumption that the operation is continuously performed. Other reactors may be used based on this idea. Alternatively, it is also possible to employ a batchwise operation.

The reaction conditions for producing NpnN' by using a batch type reactor will be described by way of example. It is suitable to use from 0.005 unit/ml to 5000 unit/ml of ATP sulfurylase. Preferably, Ap$_4$A phosphorylase is used in an amount about twice as much as that of ATP sulfurylase. It is preferable to use 10 μM or more, more preferably 1 mM or more, and most preferably 10 mM or more, of ATP or a derivative thereof. It is preferable to use 1 μM or more, more preferably 100 μM or more, and most preferably 1 mM or more, of the sulfate. Acetyl phosphate may be used as a phosphate donor. The acetyl phosphate can be used in the form of a salt such as ammonium salt, potassium/lithium salt or sodium salt. It is preferable to use disodium acetylphosphate, since it is easily obtained. Acetyl phosphate is used preferably at such a concentration that the molar ratio of acetyl phosphate to ATP or its derivative is from 1/10 to 100/1, more preferably from 1/1 to 50/1. Methods for adding these substances are not particularly restricted, and they may be added either at once at the initiation of the reaction or separate portions. Examples of the sulfate include ammonium sulfate, magnesium sulfate, sodium sulfate and potassium sulfate. PPase or metal ions such as magnesium ion, manganese ion, calcium ion, cobalt ion or cadmium ion may also be added to aid in the performance of the reaction. The PPase is preferably added in an amount of from 0.01 unit/ml to 100 unit/ml. It is also preferable to add from 1 unit/ml to 100 unit/ml of an enzyme capable of converting ADP into ATP.

The pH value in the reaction may be around the neutral point, i.e., from pH 5 to 11, preferably from pH 6 to 9. The pH value may be controlled with the use of a buffer solution. This buffer solution may be selected from among common ones which are suitable for the pH value. Examples of the buffer solution include HEPES buffers, Tris buffers, citric acid-sodium phosphate buffer, citric acid-sodium citrate buffer, $\beta,\beta'$-dimethylglutaric acid-sodium hydroxide buffer, acetic acid-sodium acetate buffer, sodium maleatesodium hydroxide buffer, phosphate buffers, imidazolehydrochloric acid buffer, triethanolamine hydrochloridesodium hydroxide buffer.

The reaction temperature is not particularly restricted, so long as enzymes are not inactivated and the reaction can smoothly proceed. A temperature range of from 20° C. to 50° C. is preferable.

The reaction product thus obtained may be purified by a method commonly employed in the art (e.g., the method described in U.S. Pat. No. 4,886,749, etc.), for example, ion exchange chromatography, to thereby isolate NpnN'.

To further illustrate the present invention in greater detail, the following examples are presented below. In these examples, the activities of ATP sulfurylase and Ap$_4$A phosphorylase were determined by the following methods.

Method for Determining ATP Sulfurylase Activity

A reaction solution of the composition specified below was maintained at 30° C. and an appropriate amount of an enzyme solution sample was added thereto to thereby initiate a reaction. After 10 minutes, 0.05 ml of 3 N sulfuric acid were added to end the reaction. After the completion of the reaction, the concentration of phosphoric acid was determined by a reagent for measuring inorganic phosphoric acid (Phospha C-Test Wako, manufactured by Wako Pure Chemical Industries, Ltd.).

The amount of ATP sulfurylase capable of giving 2 μmol of phosphoric acid, i.e., 1 μmol of pyrophosphoric acid within 1 minute was referred to as 1 unit.

| Composition of reaction solution (total volume: 0.5 ml) | |
| --- | --- |
| Tris hydrochloride buffer solution (pH 8) | 100 mM |
| magnesium chloride | 10 mM |
| sodium molybdate | 10 mM |
| ATP | 10 mM |
| pyrophosphatase | 0.4 U/ml |
| sample (ATP sulfurylase solution) | Appropriate Amount |

In the above method, it is appropriate to add $Ap_4A$ phosphorylase in such a way that the final $Ap_4A$ phosphorylase concentration in a reaction solution is less than 100 units/ml.

Method for Determining $Ap_4A$ phosphorylase activity

A reaction solution of the composition as specified below was maintained at 30° C. and an appropriate amount of an enzyme solution sample was added thereto to initiate the reaction. After 10 minutes, the reaction mixture was heated in a boiling water bath for 1 minute to end the reaction. After the completion of the reaction, the concentration of $Ap_4A$ was determined by HPLC under the conditions specified below. The amount of $Ap_4A$ phosphorylase capable of providing 1 μmol $Ap_4A$ within 1 minute was referred to as 1 unit.

| Composition of reaction solution (total volume: 0.5 ml) | |
| --- | --- |
| triethanolamine buffer solution (pH 8) | 100 mM |
| magnesium chloride | 5 mM |
| $Ap_4A$ | 1 mM |
| sample ($Ap_4A$ phosphorylase solution) | Appropriate Amount |
| potassium primary phosphate | 100 mM |
| HPLC mobile phase | |
| tetrabutylammonium perchlorate | 3 mM |
| potassium primary phosphate | 30 mM |
| methanol | 25 vol. % |
| water | 75 vol. %. |

The flow rate in the HPLC was 0.6 ml/min. The detection was carried out by measuring the UV absorbance ($\lambda = 254$ nm). A Nova Pack C18 (manufactured by Waters, octadecylsilyl silica gel was employed as the column.

In the above method, it is appropriate to add ATP sulfurylase in such a way that the final ATP sulfurylase concentration in a reaction solution is less than 500 units/ml.

REFERENCE EXAMPLE 1

A medium containing 1% of glucose, 1% of yeast extract, 0.1% of phosphoric acid, and several minerals, was sterilized and its pH was adjusted to 6.5. Then, it was inoculated with *Bacillus stearo theremophilus* (NCA 1503 strain, ATCC 29609). After incubating at 60° C. for 3 hours, it was confirmed that the glucose in the medium had been consumed. Then, the bacterial cells were collected by centrifugation.

REFERENCE EXAMPLE 2

The wet bacterial cells obtained in the above Reference Example 1 were disrupted by the freezing and thawing method and enucleated by using a polyacrylamide-series agglutinator. The precipitate thus formed was removed by centrifuging and thus a crude enzyme solution was obtained. This crude enzyme solution was applied to a DEAE-Sepharose column which had been previously equilibrated with a 50 mM Tris-HCl buffer (pH 8.0). Thus, ATP sulfurylase was adsorbed by the column. After thoroughly washing the column with the same buffer, elution was conducted by a linear gradient of from 0 to 500 mM of sodium chloride and using the same buffer. The active fraction was collected and ammonium sulfate was added in such a manner as to give a concentration of 1 M. This active fraction was applied to a Phenyl Sepharose column which had been equilibrated with a 50 mM Tris-HCl buffer (pH 8.0). After thoroughly washing the column with the same buffer, elution was conducted with a 50 mM Tris-HCl buffer (pH 8.0).

The active fraction thus obtained was collected, concentrated and dialyzed. Next, it was applied to a Matrix Gel Blue A column which had been previously equilibrated with a 50 mM Tris-HCl buffer (pH 8.0). After thoroughly washing with the same buffer, elution was conducted with the same buffer containing 1 M potassium chloride.

The active fraction was collected, concentrated and subjected to polyacrylamide gel electrophoresis. As a result, a single band was obtained.

The specific activity of this enzyme preparation was 11.1 U/mg.

REFERENCE EXAMPLE 3

A medium containing 1% of glucose, 1% of a yeast extract, 0.1% of phosphoric acid and several minerals was sterilized and its pH was adjusted to 7.2. Then, it was inoculated with *Saccharomyces cerevisiae* (IFO 1008). After incubating at 28° C. for 8 hours, bacterial cells were collected by centrifugation.

REFERENCE EXAMPLE 4

The wet bacterial cells obtained in the above Reference Example 3 were disrupted by a sonicator and enucleated by using a polyacrylamide-series agglutinator. The precipitate thus formed was removed by centrifugation and thus a crude enzyme solution was obtained. This crude enzyme solution was applied to a DEAE-Sepharose column which had been previously equilibrated with a 50 mM Tris-HCl buffer (pH 7.8). After thoroughly washing the column, elution was conducted by a linear gradient of from 0 to 500 mM of sodium chloride by using the same buffer. The active fraction was collected and thus $Ap_4A$ phosphorylase was obtained.

EXAMPLE 1

$Ap_4A$ was synthesized by a batchwise method with the use of 0.25 unit/ml of the ATP sulfurylase obtained in the above Reference Example 2 and 0.5 unit/ml of the $Ap_4A$ phosphorylase obtained in the above Reference Example 4.

A reaction mixture (a 50 mM HEPES buffer (pH 8.0) containing 15 mM of ATP and 10 mM of magnesium sulfate) was subjected to reaction at 30° C. for 6 hours.

The reaction product thus obtained was analyzed by HPLC under the same conditions as those employed for determining the activity of Ap$_4$A phosphorylase. As a result, it was found that 5.0 mM of Ap$_4$A was formed. The reaction product was identified as Ap$_4$A based on a phosphorus nuclear magnetic resonance spectrum.

EXAMPLE 2

Ap$_4$A was synthesized by a batchwise method with the use of 0.25 unit/ml of the ATP sulfurylase obtained in the above Reference Example 2 and 0.5 unit/ml of the Ap$_4$A phosphorylase obtained in the above Reference Example 4.

At the initiation of the reaction, 3.1 ml/l of acetyl phosphate was added to a reaction mixture (a 50 mM HEPES buffer (pH 7.8) containing 15 mM of ATP, 30 mM of magnesium sulfate, 0.71 unit/ml of PPase (manufactured by Boehringer Mannheim), and 0.004 unit/ml of acetate kinase (manufactured by Unitika Ltd.)). Then, the mixture was reacted at 30 °C. for 6 hours while further adding 3.1 ml/l of acetyl phosphate at intervals of 1 hour.

The reaction product thus obtained was analyzed by HPLC under the same conditions as those employed for determining the activity of Ap$_4$A phosphorylase. As a result, it was found that 6.0 mM of Ap$_4$A was formed. The reaction product was identified as Ap$_4$A based on a phosphorus nuclear magnetic resonance spectrum.

According to the present invention, highly pure NpnN', pnN or a derivative thereof can be produced at a high yield and these products can be easily isolated and purified. Thus, the present invention makes it possible to advantageously produce NpnN', pnN or a derivative thereof on an industrial scale.

While the invention has been described in detail and with reference to specific embodiment thereof, it will be apparent to one skilled in the art that various changes and modifications can be made therein without departing from the spirit and scope thereof.

What is claimed is:

1. A method for producing a dinucleoside polyphosphate, a nucleoside polyphosphate, or derivatives thereof, comprising reacting (a) adenosine-5'-triphosphate, polyphosphate, or derivatives thereof and (b) a sulfate,
    wherein said reaction takes place in the presence of (i) adenosine-5'-triphosphate sulfurylase, and (ii) diadenosine tetraphosphate phosphorylase,
    thus forming said dinucleoside polyphosphate, nucleoside polyphosphate, or derivatives thereof.

2. A method for producing a dinucleoside polyphosphate, a nucleoside polyphosphate, or derivatives thereof, comprising reacting (a) adenosine-5'-triphosphate, polyphosphate, or derivatives thereof and (b) a sulfate,
    wherein said reaction takes place in the presence of (i) an enzyme capable of converting adenosine-5'-diphosphate into adenosine-5'-triphosphate, (ii) adenosine-5'-triphosphate sulfurylase and (iii) diadenosine tetraphosphate phosphorylase,
    thus forming said dinucleoside polyphosphate, nucleoside polyphosphate, or derivatives thereof.

3. The method for producing a dinucleoside polyphosphate, a nucleoside polyphosphate or derivatives thereof as claimed in one of claims 1 or 2, wherein said dinucleoside polyphosphate is diadenosine tetraphosphate.

4. The method for producing a dinucleoside polyphosphate, a nucleoside polyphosphate or derivatives thereof as claimed in one of claims 1 or 2, wherein said adenosine-5'-triphosphate sulfurylase is an enzyme originating from a microorganism.

5. The method for producing a dinucleoside polyphosphate, a nucleoside polyphosphate or derivatives thereof as claimed in claim 4, wherein said microorganism is *Bacillus stearo thermophilus* (ATCC 29609).

6. The method for producing a dinucleoside polyphosphate, a nucleoside polyphosphate or derivatives thereof as claimed in one of claims 1 or 2, wherein said diadenosine tetraphosphate phosphorylase is an enzyme originating from a microorganism.

7. The method for producing a dinucleoside polyphosphate, a nucleoside polyphosphate or a derivative thereof as claimed in claim 6, wherein said microorganism is *Saccharomyces cerevisiae* (IFO 1008).

8. The method for producing a dinucleoside polyphosphate, a nucleoside polyphosphate or derivatives thereof as claimed in claim 2, wherein said enzyme capable of converting adenosine-5'-diphosphate into adenosine-5'-triphosphate is acetate kinase.

9. The method for producing a dinucleoside polyphosphate, a nucleoside polyphosphate or derivatives thereof as claimed in one of claims 1 or 2, wherein said reaction takes place further in the presence of pyrophosphatase.

10. The method for producing a dinucleoside polyphosphate, a nucleoside polyphosphate or derivatives thereof as claimed in one of claims 1 or 2, wherein said reaction takes place further in the presence of one or more metal ion.

11. The method for producing a dinucleoside polyphosphate, a nucleoside polyphosphate or derivatives thereof as claimed in claim 10, wherein at least one metal ion is selected from the group consisting of magnesium ion, manganese ion, calcium ion, cobalt ion and cadmium ion.

12. The method for producing a dinucleoside polyphosphate, a nucleoside polyphosphate or derivatives thereof as claimed in claim 2, wherein acetyl phosphate is used as a phosphate donor in the conversion of adenosine-5'- diphosphate to adenosine-5'-triphosphate.

13. The method for producing a dinucleoside polyphosphate, a nucleoside polyphosphate or derivatives thereof as claimed in one of claims 1 or 2, wherein the sulfate is a sulfuric acid salt.

14. The method for producing a dinucleoside polyphosphate, a nucleoside polyphosphate or derivatives thereof as claimed in one of claims 1 or 2, wherein the sulfate is at least one substance selected from the group consisting of ammonium sulfate, magnesium sulfate, sodium sulfate and potassium sulfate.

15. The method for producing a dinucleoside polyphosphate, a nucleoside polyphosphate or derivatives thereof as claimed in one of claims 1 or 2, wherein said reaction is a batch type reaction.

* * * * *